US012254962B2

(12) United States Patent
Bockelmann (10) Patent No.: US 12,254,962 B2
(45) Date of Patent: Mar. 18, 2025

(54) METHOD AND APPARATUS FOR INVESTIGATING INTRA- AND/OR INTERMOLECULAR INTERACTIONS INVOLVING RNA

(71) Applicants: Centre National De La Recherche Scientifique, Paris (FR); Ecole Superieure De Physique Et De Chimie Industrielles De La Ville De Paris, Paris (FR)

(72) Inventor: Ulrich Bockelmann, Paris (FR)

(73) Assignees: Centre National De La Recherche Scientifique, Paris (FR); Ecole Superieure De Physique Et De Chimie Industrielles De La Ville De Paris, Paris (FR)

( * ) Notice: Subject to any disclaimer, the term of this patent is extended or adjusted under 35 U.S.C. 154(b) by 917 days.

(21) Appl. No.: 17/420,195

(22) PCT Filed: Dec. 31, 2019

(86) PCT No.: PCT/EP2019/087187
§ 371 (c)(1),
(2) Date: Jul. 1, 2021

(87) PCT Pub. No.: WO2020/141171
PCT Pub. Date: Jul. 9, 2020

(65) Prior Publication Data
US 2022/0148683 A1 May 12, 2022

(30) Foreign Application Priority Data
Jan. 3, 2019 (EP) .................................... 19305004

(51) Int. Cl.
| | | |
|---|---|---|
| *G16B 99/00* | (2019.01) | |
| *C12Q 1/68* | (2018.01) | |
| *C12Q 1/6806* | (2018.01) | |
| *C12Q 1/6813* | (2018.01) | |
| *G01N 21/64* | (2006.01) | |

(52) U.S. Cl.
CPC ............ *G16B 99/00* (2019.02); *C12Q 1/68* (2013.01); *C12Q 1/6813* (2013.01); *G01N 21/6428* (2013.01); *G01N 21/6456* (2013.01); *C12Q 1/6806* (2013.01); *G01N 2021/6439* (2013.01)

(58) Field of Classification Search
CPC ...... C12Q 1/68; C12Q 1/6813; C12Q 1/6806; C12Q 2537/113; C12Q 2523/303; C12Q 2537/137
USPC .............. 435/6.1, 91.1, 91.31; 536/23.1
See application file for complete search history.

(56) References Cited

FOREIGN PATENT DOCUMENTS

EP 2311045 A1 4/2011

OTHER PUBLICATIONS

Zhang, C. et al. (2019). "The Mechanical Properties of RNA-DNA Hybrid Duplex Stretched by Magnetic Tweezers." Biophysical J. 116. 196-204. (Year: 2019).*
Bockelmann, U., et al., "Molecular stick-slip motion revealed by opening DNA with piconewton forces", Physical Review Letters, Dec. 1, 1997, pp. 4489-4492, vol. 79, No. 22, American Physical Society, US.
Bockelmann, U., et al., "Unzipping DNA with Optical Tweezers: High Sequence Sensitivity and Force Flips", Biophysical Journal, Mar. 2002, pp. 1537-1553, vol. 82, No. 3, Cell Press, US.
Bockelmann, Ulrich, "Single-molecule manipulation of nucleic acids", Current Opinion in Structural Biology, Jun. 2004, pp. 368-373, vol. 14, No. 3, Elsevier, Ltd., UK.
Geffroy, Laurent, et al., "Chapter 2: RNA Unzipping and Force Measurements with a Dual Optical Trap", *Single Molecule Analysis*, Erwin J.G. Peterman, Editor, Sep. 23, 2017, pp. 25-41, Second Edition, Humana Press, US.
Gross, Peter, et al., "Quantifying how DNA stretches, melts and changes twist under tension", Nature Physics, Sep. 2011, pp. 731-735, plus 16 pages of Supplementary Information, vol. 7, Macmillan Publishers Limited, UK.
Haentjens-Sitri, Julie, et al., "A competition mechanism regulates the translation of the *Escherichia coli* operon encoding ribosomal proteins L35 and L20", Journal of Molecular Biology, 2008, (published online Nov. 1, 2007), pp. 612-625, vol. 375, Elsevier Ltd., UK.

(Continued)

*Primary Examiner* — Jane J Zara
(74) *Attorney, Agent, or Firm* — HAUPTMAN HAM, LLP (57) ABSTRACT

A method for investigating intra- and/or intermolecular interactions involving RNA is provided. The method includes a) synthesizing a RNA/DNA heteroduplex (RDH) comprising a RNA strand of interest paired to a DNA strand; b) binding a first end of the DNA strand and a corresponding first end of the RNA strand to a first element of a nanoscale manipulating device, and a second end of the DNA strand to a second element of the nanoscale manipulating device, leaving a second end of the RNA strand free; c) moving the first and second elements of the manipulating device apart from each other, stretching the DNA strand and causing the RNA strand to peel off the heteroduplex; and d) moving the first and second elements of the nanoscale manipulating device towards each other, allowing the DNA strand to relax and causing the RNA strand to bind again to it. Measurement of a force-displacement relationship during steps c) and d) provides information on intra- and/or intermolecular interactions involving the RNA strand. Also provided is an apparatus for carrying out the method.

11 Claims, 7 Drawing Sheets

Specification includes a Sequence Listing.

(56) References Cited

OTHER PUBLICATIONS

Heller, Iddo, et al., "STED nanoscopy combined with optical tweezers reveals protein dynamics on densely covered DNA", Nature Methods, Sep. 2013, pp. 910-916, plus 3 pages of Supplemental Information, vol. 10, No. 9, Nature America, Inc., US.

Laszlo, Andrew H., et al., "MspA nanopore as a single-molecule tool: From sequencing to SPRNT", Methods, Aug. 1, 2016, pp. 75-89, vol. 105, Elsevier Inc., US.

Lewicki, Birgit T. U., et al., "Coupling of rRNA transcription and ribosomal assembly in vivo", Journal of Molecular Biology, Jun. 5, 1993, pp. 581-593, vol. 231, No. 3, Academic Press Limited, UK.

Lisica, Ana, et al., "Optical tweezers studies of transcription by eukaryotic RNA polymerases", Biomolecular Concepts, Jan. 2017, pp. 1-11, vol. 8, No. 1, European Patent Office, De Gruyter, Germany.

Mangeol, Pierre, et al., "Interference and crosstalk in double optical tweezers using a single laser source", Review of Scientific Instruments, Aug. 2008, pp. 083103-1-083103-8, vol. 79, No. 9, American Institute of Physics, US.

Neuman, K. C., et al. "Single-Molecule Micromanipulation Techniques", Annual Review of Materials Research, Aug. 4, 2007, pp. 33-67, vol. 37, Annual Reviews, US.

Odijk, Theo, "Notes: Stiff Chains and Filaments under Tension", Macromolecules, Sep. 1, 1995, pp. 7016-7018, vol. 28, No. 20, ACS Publications, US.

Smith, Steven B., et al., "Overstretching B-DNA: The elastic response of individual double-stranded and single-stranded DNA molecules", Science, Feb. 9, 1996, pp. 795-799, vol. 271, No. 5250, American Association for the Advancement of Science, US.

Stephenson, William, et al., "Nanomanipulation of Single RNA Molecules by Optical Tweezers", Journal of Visualized Experiments, Aug. 20, 2014, No. 90, article e51542, 18 pages, MyJove Corp., US.

Wang, Michelle D., et al., "Stretching DNA with optical tweezers", Biophysical Journal, Mar. 1997, pp. 1335-1346, vol. 72, No. 3, Elsevier Inc., U.S.

Zhang, Chen, et al., "The Mechanical Properties of RNA-DNA Hybrid Duplex Stretched by Magnetic Tweezers", Biophysical Journal, Jan. 22, 2019, pp. 196-204, vol. 116, Elsevier Inc., U.S.

Zhang, Chen, et al., "Supplemental Information: The Mechanical Properties of RNA-DNA Hybrid Duplex Stretched by Magnetic Tweezers", Biophysical Journal, Jan. 22, 2019, 6 pages, Elsevier Inc., U.S., retrieved from the Internet: <URL:https://ars.els-cdn.com/content/image/1-s2.0-S0006349518344722-mmc1.pdf>, retrieved on Jun. 21, 2019.

European Patent Office, Extended European Search Report received for Application No. 19305004.4, dated Jul. 3, 2019, 9 pages, Germany.

International Searching Authority, International Search Report and Written Opinion received for International Application No. PCT/EP2019/087187, dated Mar. 19, 2020, 13 pages, European Patent Office, Netherlands.

* cited by examiner

METHOD AND APPARATUS FOR INVESTIGATING INTRA- AND/OR INTERMOLECULAR INTERACTIONS INVOLVING RNA

CROSS-REFERENCE TO RELATED APPLICATIONS

The present application is a national phase entry of PCT/EP2019/087187, filed on Dec. 31, 2019, which claims the benefit of priority of European Application No. 19305004.4, filed Jan. 3, 2019, the entire contents of which are hereby incorporated by reference in their entirety for all purposes.

FIELD

The invention relates to a method and to an apparatus for investigating in vitro intermolecular and intramolecular interaction involving RNA. By "intramolecular interactions" it is meant chemical interactions, such as covalent or non-covalent bonds, between different parts of a same RNA chain or strand, which are responsible for the secondary and tertiary structure of RNA—e.g. helices, hairpins, pseudo-knots etc. By "intermolecular interactions" it is meant chemical interactions, such as covalent or non-covalent bonds, between a RNA chain or strand and other molecules such as proteins (e.g. ribosomal proteins) and RNA-targeting drugs (e.g. some antibiotics).

BACKGROUND

RNA plays many essential roles in the cell physiology. First and foremost, messenger RNA (mRNA) conveys genetic information and directs the synthesis of proteins, cooperating with transport RNA (tRNA). Other RNA molecules catalyzes biological reactions (ribozymes), control gene expression etc. RNA is also an essential component of ribosomes, the complex molecular machines that serves as the site of protein synthesis in cells.

Like DNA, RNA is a linear polymer, i.e. a chain, of nucleotides. Each nucleotide consists of three elements: a pentose sugar (ribose, for RNA), a phosphate group and a nucleobase. Unlike DNA, however, RNA most often occurs in single-stranded form. Like other biological macromolecules, RNA strands usually adopt a well-defined three-dimensional shape (tertiary structure) for which the pattern of hydrogen bonds within the molecule (secondary structure) is an important determinant. The three-dimensional shape strongly influences the biological activity of the RNA molecule. Moreover, in some cases RNA forms complexes with other molecules—notably proteins. Among the most important of such complexes are ribosomes and spliceosomes.

Due to its multiple and essential roles in cell metabolism, RNA is targeted by many drugs, e.g. some antibiotics. The interactions of these drug molecules with RNA chains determine their activity.

Therefore, it is of utmost importance for research in molecular biology and pharmacology to precisely characterize intra- and inter-molecular interactions involving RNA.

These interactions are usually studied by performing experiments in vitro, but transposing the results thus obtained to the actual in vivo interaction mechanisms is far from trivial. This appears clearly in the case of ribosome assembly.

In E. coli, ribosome biogenesis in vivo can occur efficiently at temperatures of ≤37° C. in a couple of minutes, while in vitro ribosome reconstitution takes much longer (50S subunits: 90 minutes at 50° C.). It has been suggested that this is at least partly due to the fact that in vivo ribosome assembly occurs co-transcriptionally, i.e. ribosomal proteins and assembly factors bind to the rRNA (ribosomal RNA) during its transcription, while in vitro it is pre-synthesized rRNA which interacts with ribosomal proteins and assembly factors.

There are reasons to believe that, more generally, RNA folding and other intra- and inter-molecular interactions occur co-transcriptionally, which affects their kinetics and the three-dimensional structure of the resulting RNA molecules or RNA-based complexes.

Some in vivo studies of such interactions have been performed. For instance, Lewicki et al have investigated [Lewicki 1993] in vivo the coupling between rRNA transcription and ribosomal assembly. This approach, however, is cumbersome and cannot be easily generalized.

Therefore, there is a need for a method of performing in vitro investigation of RNA intra- and intermolecular interaction mimicking in vivo conditions, where RNA gradually emerges by transcription.

BRIEF SUMMARY

The invention aims at providing such a method, and an apparatus for implementing it.

An object of the present invention, allowing achieving this aim, is a method for investigating intra- and/or intermolecular interactions involving RNA, comprising the steps of:
  a) synthesizing a RNA/DNA heteroduplex comprising a RNA strand of interest paired to a DNA strand, each of said strands having a first and a second end;
  b) binding a first end of the DNA strand and a corresponding first end of the RNA strand to a first element of a nanoscale manipulating device (typically, dual-trap optical tweezers), and a second end of the DNA strand to a second element of the nanoscale manipulating device, leaving a second end of the RNA strand free;
  c) moving the first and second elements of the manipulating device apart from each other, stretching the DNA strand and causing the RNA strand to peel off the heteroduplex, while measuring a force-displacement relationship; and
  d) moving the first and second elements of the nanoscale manipulating device towards each other, allowing the DNA strand to relax and causing the RNA strand to bind again to it, while continuing measuring the force-displacement relationship;
  wherein at least one of step c) and d) is carried out while controlling said moving of the first and second elements of the manipulating device in such a way that an end-to-end distance of the heteroduplex varies according to a predetermined time law.

The force-displacement relationship measured during steps c) and d) provides information on intra- and/or intermolecular interactions involving the peeled RNA strand.

The peeling of the RNA strand occurs gradually, simulating the transcription process, which occurs naturally in vivo. Unlike in actual in vivo experiments, however, the investigator has fully control of the physical and chemical environment of the process (e.g. the presence of molecules suitable to bind to RNA, such as ribosomal proteins, small RNAs (sRNA), riboswitch ligands or candidate drugs), of the speed at which the RNA emerges and, more generally, of most parameters suitable to have an influence on the relevant interactions. Small RNA (sRNA) are non-coding RNA molecules that exhibit a length typically not exceeding 200 nucleotides.

Another object of the invention is an apparatus for investigating intra- and/or intermolecular interactions involving RNA, comprising:
- a fluidic chamber adapted for holding a liquid solution containing a RNA/DNA heteroduplex comprising a RNA strand of interest paired to a DNA strand, each of said strands having a first and a second end;
- a nanoscale manipulating device (e.g. dual-trap optical tweezers) having a first and second parts, moveable with respect to each other, the first part being adapted for binding to the first end of the DNA strand and to the first end of the RNA strand and the second part being adapted for binding to the second end of the DNA strand;
- a measurement device for measuring a force-displacement relationship of the nanoscale manipulating device; and
- an electronic data processing system configured or programmed for:
  - driving the nanoscale manipulating device by moving the first and second elements of the manipulating device apart from each other and then by moving the first and second elements of the nanoscale manipulating device towards each other, said moving being performed in such a way that an end-to-end distance of the heteroduplex varies according to a predetermined time law;
  - acquiring measurement data from the measurement device while driving the nanoscale manipulating device; and
  - obtaining information on intra- and/or intermolecular interactions involving the RNA strand by analyzing the acquired measurement data.

Particular embodiments of the invention constitute the subject-matter of the dependent claims.

Dual-trap (or dual-beam) optical tweezers have already been used to overstretch double-strand DNA, and even inducing peeling of a free-ended strand thereof. See [Gross et al. 2011]. However, this technique has only been used for investigating mechanical properties of DNA, and its application to the investigation of molecular interactions—let alone interactions involving RNA—is not straightforward, and requires non-trivial adjustments, such as the use of RNA/DNA heteroduplexes.

Moreover, experiments involving stretching and peeling RNA/DNA duplexes have already been performed by [Zhang et al. 2019]. The aim, however, was to study the mechanical properties of the duplexes themselves, not the intra- and/or intermolecular interactions involving a RNA strand. And indeed, the method used by these authors was not suitable to study such interactions.

BRIEF DESCRIPTION OF THE SEVERAL VIEWS OF THE DRAWING(S)

Additional features and advantages of the present invention will become apparent from the subsequent description, taken in conjunction with the accompanying drawings, wherein.

DETAILED DESCRIPTION

FIGS. 1A to 1E schematically illustrate the different steps of a measurement according to the invention.

First of all, a RNA-DNA heteroduplex (reference RDH on FIG. 1) is synthesized. The hetheroduplex comprises a RNA strand RS with a predetermined nucleotide sequence, whose intra- and/or inter-molecular interactions have to be investigated, and a complementary DNA strand DS. The 5' end of the DNA strand and the 3' end of the RNA strand are bound to a first micrometer-sized dielectric bead DB1, and the 3' end of the DNA strand is bound to a second micrometer-sized dielectric bead DB2, while the 5' end of the RNA strand is left free. The resulting construct is illustrated on FIG. 1A; a protocol for synthesizing it will be described later. The construct is immersed in a saline solution which may contain molecules suitable to interact with the RNA strand, e.g. ribosomal proteins or RNA-targeting drugs or candidate drugs.

Figure 1A:
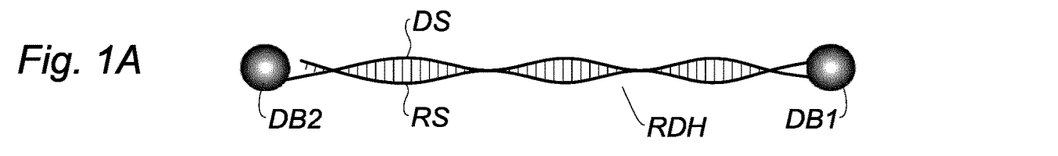
FIGS. 1A to 1E schematically represent a RNA/DNA heteroduplex through different stages of a method according to an embodiment of the invention.
Figure 1B:
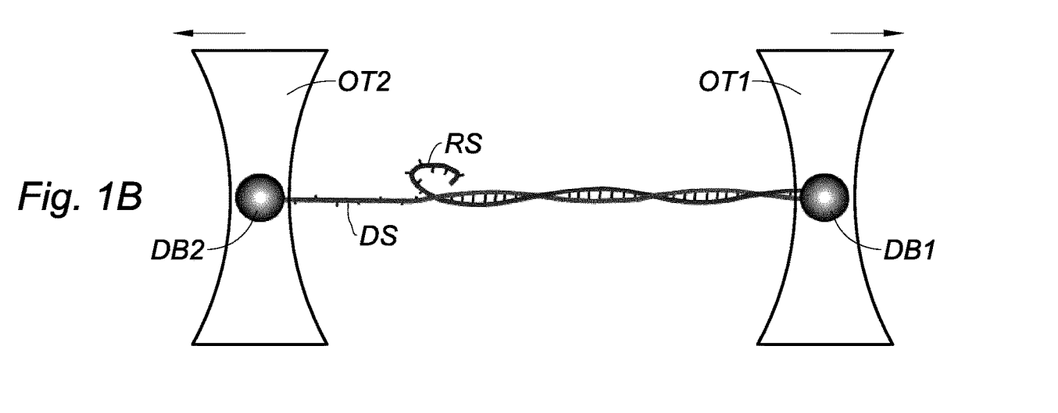
Figure 1C:
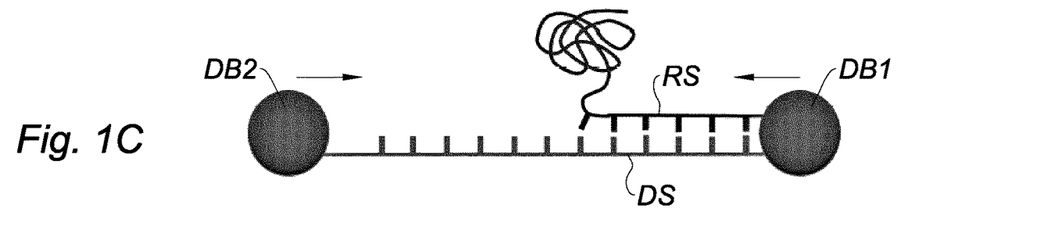
Figure 1D:
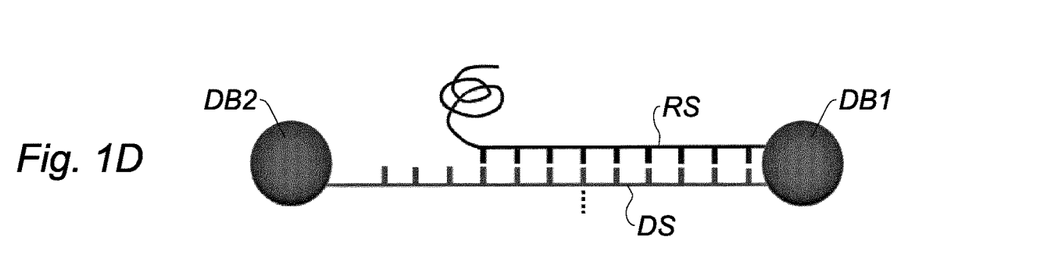
Figure 1E:
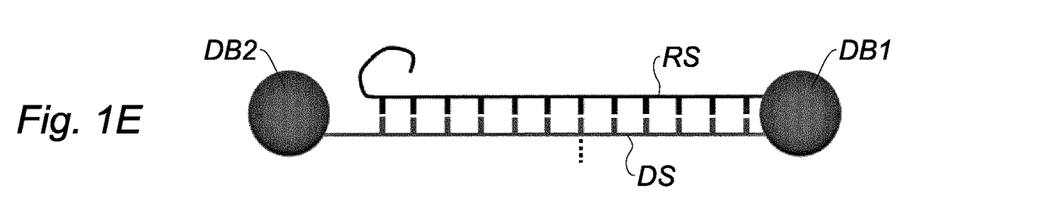

The two dielectric beads are captured in two separate optical traps OT1, OT2, represented in FIG. 1B (the optical traps are not represented in FIGS. 1C-1E, but they are nevertheless present). The two optical traps are used to move the dielectric beads apart from each other, stretching the heteroduplex RDH. At some points, for a traction force exceeding 60 pN (pico Newton), the RNA strand starts to peel off the DNA strand starting from its free end and folds due to the intramolecular interactions between nucleotide of different regions of its chain and/or intermolecular interactions with molecules contained in the solution, forming secondary and tertiary structures. The peeling front propagates in a one-dimensional manner through the base sequence, which explains the appearance of a plateau in the force—displacement relationship. In this situation, the theoretical description of the sequence-dependent force signals is related to the description of nucleic acid unzipping (see [Gross et al. 2011], [Bockelmann 1997, [Bockelmann 2002]). Sequence regions exhibiting high (low) GC content lead to high (low) force. Molecular stick-slip dynamics induces sawtooth-like features in the force-displacement curves. Typically, the peeling front advances little in front of a sequence with increasing GC content. During this 'stick' phase force rises slowly. Subsequently a 'slip' event occurs once the local energy barrier is overcome. Then the peeling front advances rapidly and the force drops. The energy landscape is determined by the base sequence, but the exact positions where the transitions occur exhibit stochastic variation.

The progress of the peeling is determined by the imposed displacement. A displacement of about 0.20 nm corresponds to peeling one RNA nucleotide. The value of this correspondence can be determined precisely for each experimental condition (type of salts and their concentrations, temperature) by peeling a construct entirely, from the first to the last nucleotide. The ratio x/N of the displacement x imposed between the beginning and the end of the peeling plateau and the known number N of base pairs of the heteroduplex, then provides the displacement per peeled RNA nucleotide at the experimental condition.

The peeled-off RNA strand "emerges" from the heteroduplex like, in vivo, transcribed RNA emerges from a RNA polymerase complex. Like in vivo, the 5' end emerges first (however, for some investigation, it may be interesting to have the 3' end emerge first, in which case the 5' end of the RNA strand would be bound to the first bead DB1 and the 3' end would be left free).

As it is known in the art, a force-displacement relationship is obtained by measuring the position of one bead within the trap to nanometer precision, while the other trap is displaced. The force-displacement relationship measured during traction can be related to the base sequence of the heteroduplex, using a theoretical description as described in [Gross et al. 2011]. This way the position of a local (peak or valley) structure in the force plateau can be attributed to a base pair index to a precision that can approach a single base pair. The force displacement curve recorded during the peeling process thus provides a precise relation between the imposed displacement and the position within the nucleotide sequence.

After that a predetermined maximum displacement, and therefore stretching, has been achieved, the optical traps are used for moving the beads towards each other, resulting in a relaxation of the partially (or totally) undone heteroduplex (FIGS. 1C, 1D and 1E). The relaxation can lead to three different issues: the single-strand that was peeled off to a certain length may stay entirely single-stranded ("no anneal, FIG. 1C), it may re-anneal to a certain position in its base sequence and then remain single-stranded ("partial anneal, FIG. 1D); or it may re-anneal to full-length, giving rise to the initial double-stranded configuration (FIG. 1E). This is due to the secondary/tertiary structures formed in the single strand RNA as well as to the proteins or other molecules bound to it, which can delay, hinder or entirely preclude the re-annealing.

During the relaxation, too, the force-displacement relationship is measured again. This force-displacement relationship is different from the one measured during the stretching phase, precisely because of the structures and molecular bonds which affect the re-annealing. For instance, a delayed or entirely precluded re-annealing manifests itself by a smooth decrease in force, which follows a line that can be extrapolated to higher force in order to compare it to the signal recorded upon peeling—see the dashed lines on FIG. 6. For this extrapolation, well-known theoretical descriptions of the elasticity of single-stranded DNA and RNA-DNA duplexes ([Gross et al. 2011], [Smith 1996], [Wang 1997], [Odijk 1995]) can be employed. This way, the force signal recorded upon distance reduction, which consists of a series of smooth decreases in force and sudden force increases, can be related to a pattern of stable structures (e.g. particularly stable helices and tertiary structure interaction for bare RNA or protein-stabilized RNA structure for RNA in the presence of proteins). The positions of the different stable structures within the nucleotide sequence are determined by the extrapolation to and comparison with the force signal recorded upon peeling.

Figure 2:
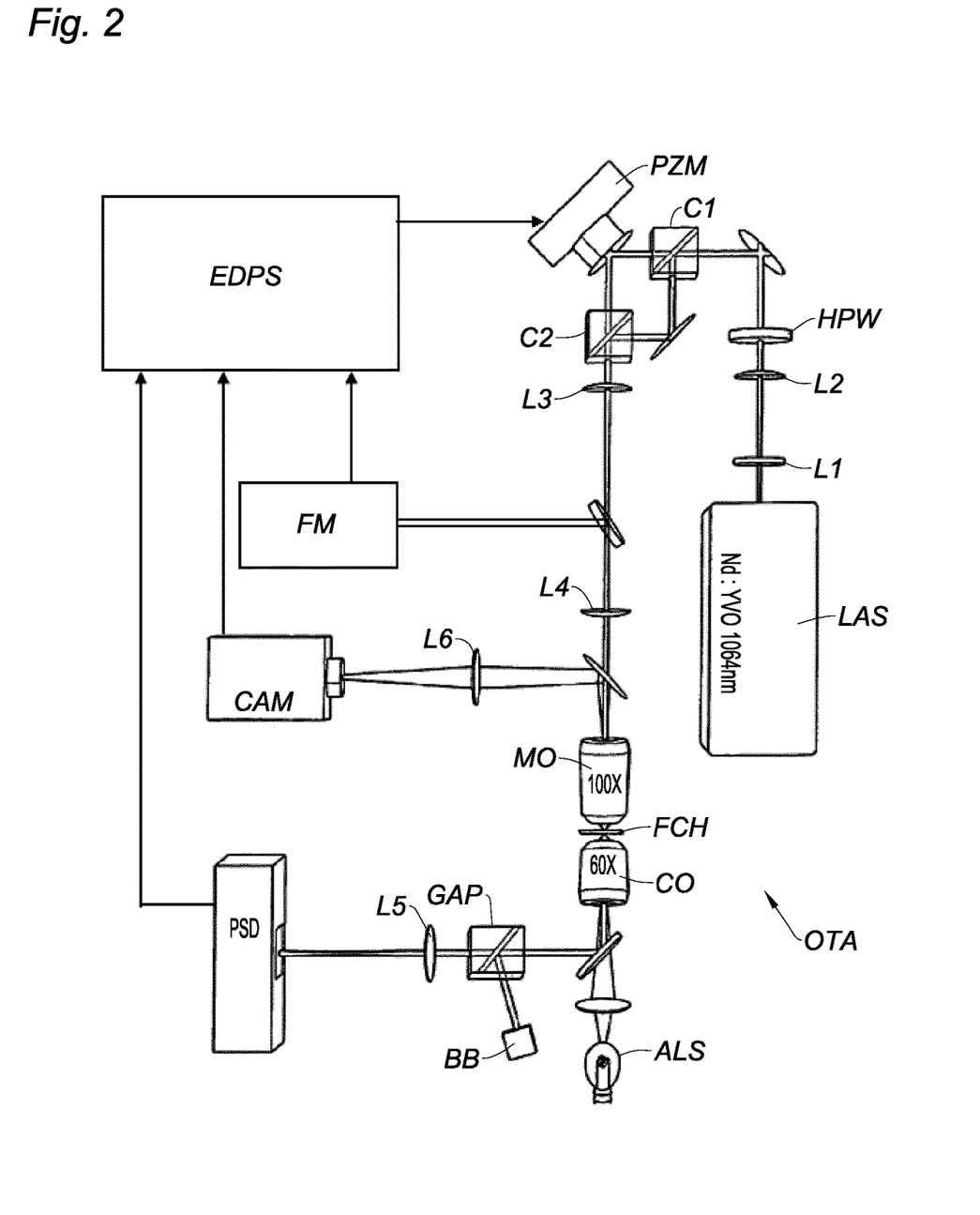
FIG. 2 illustrates an apparatus according to an embodiment of the invention.

The experimental apparatus OTA illustrated on FIG. 2, which generates and actuates dual-trap optical tweezers, is based on a custom-designed inverted microscope. For optical trapping and force detection, the apparatus comprises, here, a CW linearly polarized diode pumped Nd:YVO$_4$ laser LAS (1.064 µm, 10 W). The laser beam is first expanded through a beam expander comprising two lenses L1 and L2).

Then, in order to create two independent traps, the laser beam is split by polarization by the combination of a half-wave plate HPW and a first polarizing cube beamsplitter C1. The direction of one of the two beams is varied by a piezoelectric mirror mount PZM with integrated position sensor operating in feedback loop. After recombination with a second polarizing cube beamsplitter C2, the two beams exhibit perpendicular polarization and their directions are slightly tilted to obtain two separate traps. Lenses L3 and L4 form a beam steering and image the center of the mirror mounted on the piezoelectric stage on a back focal plane of a trapping microscope objective MO. The beams are then collimated by a second objective or condenser CO. A fluidic chamber FCH containing the sample (a volume of saline solution containing beads-bound heteroduplexes and possibly molecules suitable to interact with RNA, such as ribosomal proteins RSP) is situated between the microscope objective MO and the condenser CO. As illustrated on FIG. 3, the fluidic chamber FCH is composed of two glass coverslips sealed together by two parallel parafilm layers. The chamber is filled with a pipet P, then its two open edges are sealed with wax. Finally, a Glan-air polarizer GAP reflects one of the two beams, directing it to a beam stop BB, while the other beam goes through a lens L5 which images the back focal plane of the second objective on a position sensitive detector PSD. As it can be seen on FIG. 2, a part of the optical path of the apparatus according to the invention is also used to image the sample—which is illuminated through the condenser CO by an auxiliary light source ALS, on a CCD camera CAM. The camera allows to ensure that the two beads fixed to a molecule are trapped by the laser beam before starting the measurement. In order to avoid fluctuations from air currents, the optical path is fully enclosed. Most mechanical parts are designed to reduce drift and vibration. In variant, any other suitable polarizer can be used in place of the Glan-air polarizer.

Force measurements in optical tweezers generally use either laser light going through the particle or bead, trapped by the first objective, for interferometric position detection or white light illumination for video based detection. The apparatus of FIG. 2 uses back focal plane interferometry to measure the force. The method implemented consists in evaluating the pattern of laser light diffracted by one of the trapped beads in the back focal plane of the condenser (or second objective) CO by imaging the pattern on a four-quadrant photodiode or any other suitable position sensitive detector (PSD).

As the two beams entering the trapping objective are of perpendicular polarization, if one wants to separately detect the position of one of the beads in its trap, one has to split by polarization the beams used to trap. Since a linearly polarized beam suffers from a non-homogeneous rotation of polarization when going through the optical components of a microscope, the discrimination of the two beams according to polarization cannot be perfectly achieved. If the polarization of one beam is checked after the back focal plane of the second objective with the polarizer, it can be observed that the transmitted light pattern exhibiting a polarization perpendicular to the incident beam is cross-shaped. Consequently, the rotation of polarization allows for interference between the two beams, and the crosstalk that occurs is not simply the sum of the signals coming from the two beams separately.

More details on the apparatus of FIG. 2 can be found in EP 2 311 045 and [Mangeol 2008].

An electronic data processing system EDPS drives the piezoelectric mirror mount PZM in closed-loop to move the optical trap apart from each other (in order to stretch the heteroduplex) or towards each other (to anneal it) in a controlled way. Moreover, it receives and processes measurement data issued by the position sensitive detector PSD, and possibly by the camera CAM, and analyzes these data for obtaining information on the intra- and/or intermolecular interactions involving the RNA strand under investigation, as explained above. The electronic data processing system EDPS may comprise one or more suitably-programmed computers and/or microprocessors or microcontrollers, and possibly customized electronic circuits.

In the embodiment of FIG. 2 a fluorescence microscope FM—e.g. a confocal microscope—images the sample through the objective MO, the acquired images being processed by the electronic data processing system EDPS. The microscope allows taking wide-field, confocal or super-resolution fluorescence images of fluorescent molecules binding to the single-strand RNA (these molecules may be intrinsically fluorescent, or marked with a fluorophore). The images allow precisely identifying the molecules binding at specific sites of the RNA, whose presence is also detected by analyzing the force-displacement curve acquired during the re-annealing phase of the inventive method. Combining super-resolution fluorescence microscopy (in particular, STED) with optical tweezers is known from [Heller 2013]. The fluorescence microscope may also be used to take an image of the heteroduplex after a peeling—annealing cycle, showing molecules bound to the RNA basis.

Figure 4:
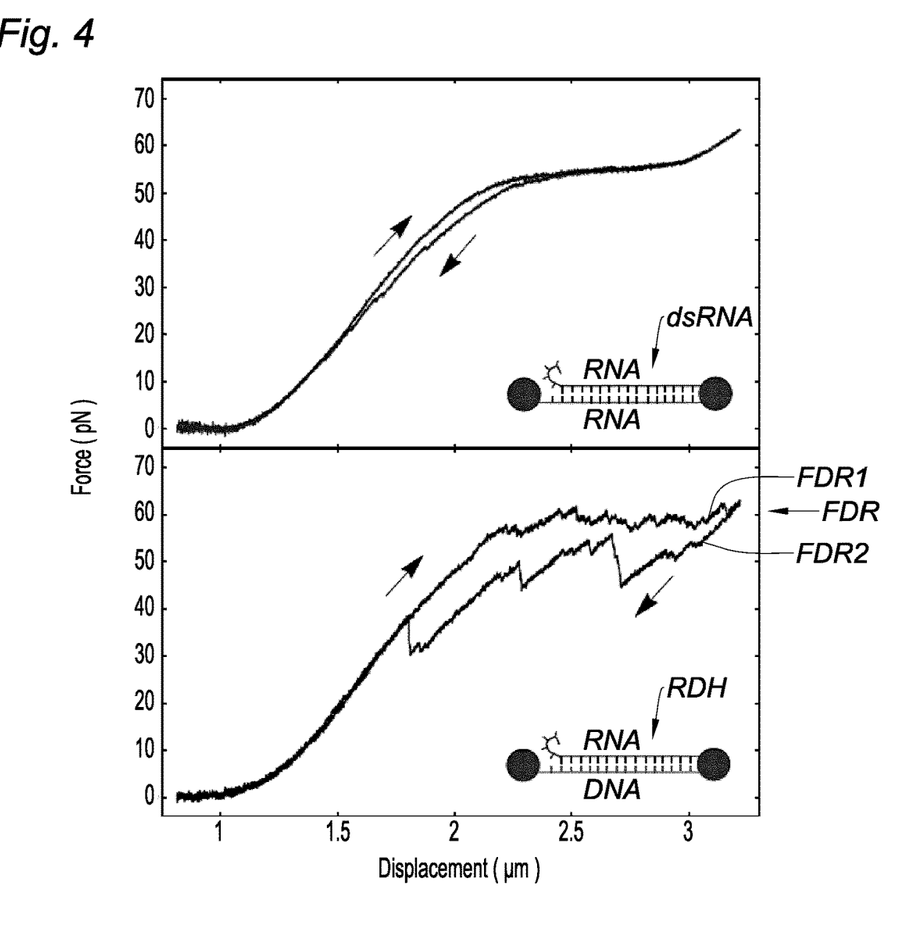
FIG. 4 shows experimental results highlighting the importance of using a RNA/DNA heteroduplex.

FIG. 4 shows the measured force-displacement relationships FDR for two different duplexes: a double stand RNA—dsRNA—(upper panel) and a RNA/DNA heteroduplex RDH (lower panel). Arrows indicate the direction of imposed displacement; a curve FDR1 measured upon pulling and the curve FDR2 measured upon subsequent retraction is shown in each case. The molecular duplexes and their three-point attachments to the two beads are schematically represented in the insets. Every duplex exhibits one 5' extremity that is free to peel off. The two measurements have been performed under same buffer condition (100 mM KCl, 5 mM MgCl2, 20 mM Hepes, pH 7.6) and at same displacement velocity (100 nm/s). The RNA strand with a free extremity is the same in both cases: it contains 4050 pairs and corresponds to the sequence of a portion of the *E. coli* chromosome (strain K-12, substrate MG1655) starting at the first nucleotide of the rrlB gene (coding for 23S rRNA), encompassing the full gene sequences of rrlB and rrfB (coding for 5S rRNA) and ending in the middle of the murB gene.

For both dsRNA and the RNA/DNA heteroduplex, the force-displacement relationship shows a force which increases slowly for small displacement and then increasingly quickly, before plateauing in the "overstretch" regime.

Surprisingly strong qualitative differences are observed between the overstretching curves of the dsRNA duplex and of the RNA/DNA heteroduplex. For dsRNA, the plateau is smooth and exhibits rather small hysteresis, whereas for the RNA/DNA heteroduplex force/displacement curve reveals a succession of sawtooth-shaped peaks and a strong hysteresis with deep decreases in force followed by sudden returns. This indicates that, when overstretched, dsRNA straightens but does not peel, thus does not expose local single-stranded RNA sequences. This is probably due to the higher base pair binding ($E_b$=3.33 kBT) of dsRNA as compared to the RNA/DNA heteroduplex (2.38 kBT). The consequence is that dsRNA cannot be used to carry out the inventive method, hence the use of a RNA/DNA heteroduplex.

EXAMPLES

An exemplary embodiment of the inventive method and its application to the early stage of *E. coli* large ribosomal subunit assembly will now be described in detail.

The RNA strand of interest consisted of a sequence of 1200 nucleotide from the 5' of the 23S RNA of *E. coli*, forming what is called 12S, or domains I and II.

First of all, the RNA/DNA heteroduplex (or "hybrid") containing this RNA strand was synthesized, and three extremities of it (both extremities of the DNA strand and the 3' extremity of the RNA strand) were modified by incorporation of biotin-carrying nucleotides, while the 5' extremity of the RNA strand was left unmodified. Since biotin makes a strong non-covalent bond with streptavidin, the incorporation of biotin-carrying nucleotides allowed the modified extremities to attach to streptavidin-functionalized beads DB1, DB2, while the unmodified extremity remained free. The two beads were then trapped in two optical tweezers and moved apart, as discussed above.

The RNA-DNA hybrid with three biotin modified extremities was prepared in three steps. At first, a biotin modified dsDNA carrying the DNA strand of interest was prepared. Then, the RNA leading strand was prepared by in vitro transcription (IVT) and to finalize, the RNA strand and dsDNA were combined to do a strand exchange by hybridization.

The dsDNA was prepared as follows (steps A1-A5):
A1 Polymerase Chain Reaction (PCR)

The sequence of interest (4050 bp) containing the genes rrlB (coding for 23S rRNA), rrfB (coding for 5S rRNA) and 1/2 murB was amplified by polymerase chain reaction (PCR) from pT7-rrnB plasmid (provided by Knud Nierhaus). The PCR primers were designed to introduce a sequence of T7 RNA polymerase and a restriction site for AflII restriction enzyme in one extremity of the PCR product (F-MB forward primer), and a restriction site for FseI restriction enzyme in the other extremity. PCR yield and stability were improved by addition of betaine (1M final concentration) and single stranded DNA binding protein ET-SSB (200 ng final amount). For PCR, 250 µl of reaction solution was prepared containing the following products:

12.5 µl of 10 µM F_MB forward primer (5'→3' TAA-TAC-GAC-TCA-CTA-TAG-GGA-GA-C-AAT-TG-C-TTA-AG-G-GTT-AAG-CGA-CTA-AGC-GTA-C, Eurogentec)

12.5 µl of 10 µM R_MB reverse primer (5'→3' C-CAC-TGA-ATT-GAG-CAG-ACC-C-GG-CCG-G-AG-AGG-ATC-GAT-CAG-ACT-AAT-CAT, Eurogentec)

- 5 µl mix of 10 mM each dATP, dGTP, dCTP, dTTP (catalog #N04465, NEB)
- 2 µl of pT7-RB plasmid (IBPC) with concentration of 16.3 ng/µl
- 2.5 µl Q5 ® High-Fidelity DNA Polymerase with 2000 units/ml concentration (catalog #M0491S, New England Biolabs)
- 50 µl of Q5 ® Reaction Buffer (initial concentration 5×) to have 1× final concentration (catalog #B9027S, New England biolabs)

50 µl of 5M Betaine solution (catalog #B0300-1VL, Sigma Aldrich)

4 µl of ET-SSB single-stranded DNA binding protein with concentration of 500 µg/ml (catalog #M2401S, New England Biolabs)

111.5 µl of distilled water.

The reaction solution was homogenized gently with a pipet and then distributed into five 200 µl PCR tubes to have 50 µl solution in each. The tubes with the reaction solution were then incubated in the thermo-cycler and went through the following thermal cycle:

98° C.: 30"
98° C.: 10"
66° C.: 30"×30
72° C.: 1'30"
72° C.: 5'

After incubation the PCR product was purified using Monarch® PCR & DNA Cleanup Kit (5 µg) (catalog #T1030S).

Part of purified PCR product was conserved for in vitro RNA transcription and the other part was used to perform a restriction by FseI restriction enzyme.

A2 FseI Restriction

Restriction of dsDNA (PCR product) by FseI restriction enzyme (catalog #R0588S, New England Biolabs) generates a 4 nucleotide long overhang at the 3' extremity of the leading strand, i.e. a sticky end in the dsDNA. The sticky end allows replacing the restricted parts of the leading and legging strands by two DNA oligonucleotides carrying biotin modifications. The amount recommended by New England Biolabs (NEB) for the FseI enzyme is 5 units per 1 µg of dsDNA and the recommended maximum reaction volume is 50 µl. The efficiency of the enzyme is higher in ≤50 µl volumes. Therefore the following reaction solution was prepared:

1 µg of dsDNA (purified PCR product)

1× CutSmart buffer (initial concentration 10×, catalog #B7204S, NEB)

20 µg BSA (Bovin Serum Albumin), Molecular Biology Grade (initial concentration 20 mg/ml, catalog #B9000S, NEB)

5 units of FesI restriction enzyme (initial concentration 2000 units/ml, catalog #R0588S, NEB).

Distilled water to adjust the reaction volume to 50 µl (if required).

The reaction mix was then homogenized by a pipet and was incubated 4 h at 37° C. After incubation the restricted sample was purified using Monarch® PCR & DNA Cleanup Kit (5 µg) (catalog #T1030S) and was ready for ligation of two biotin modified DNA oligonucleotides: one (sur_compDNA2biot_MB) at the 3' extremity of the leading strand and the other one (sur_DNAbiot_MB) at the 5' extremity of the lagging strand.

A3 Ligation of Sur DNAbiot MB and Sur_compDNA2biot_MB Oligonucleotides

For successful ligation in reaction mix it is required to have DNA oligonucleotides 30× in excess in molarity compared to restricted by FseI dsDNA product, e.g. for 1 pmol dsDNA 30 pmols of each oligonucleotide. Besides, as in the case of restriction, ligation enzymes act more efficiently in ≤50 µl reaction volumes. To prepare 50 µl reaction solution the following ingredients were mixed:

1 pmol dsDNA (purified after the digestion by FseI)

30 pmols sur_DNAbiot_MB (5'→3' Phosphate CCT-CTC-CTA-GCT-AGT-CTGATT-AGT-AGC-GCA-nCA-GG-biot, n = biotin-dT 684.70, Eurofins Genomics)

30 pmols sur_compDNA2biot_MB (5'→3' GGC-CGG-AGA-GGA-TCG-ATC-AGACTA-ATC-ATC-GCG-nAG-nCC-biot, n = biotin-dT 684.70, Eurofins Genomics)

1× T4 DNA ligase buffer (10× initial concentration, catalog #B0202S, NEB)

1812 units of T4 DNA ligase (with 400000 units/ml initial concentration, catalog #M0202S, NEB)

Distilled water to adjust the final volume to 50 µl (if required).

The reaction solution was homogenized by a pipet and was incubated 4 h at 37° C. After incubation, the sample was purified using Monarch® PCR & DNA Cleanup Kit (5 µg) (catalog #T1030S) and was ready for the next restriction step: restriction by AflIII restriction enzyme.

A4 AflIII Restriction

Restriction of purified after ligation step dsDNA product generates four nucleotide long overhang (5'→3' TTAA) at the 5' end of the leading strand. For high efficiency of restriction, the recommended amount of AflIII restriction enzyme (with initial concentration of 20000 units/ml, catalog #R0520S, NEB) is 5-10 units per 1 µg of dsDNA, and the recommended volume is ≤50 µl. In our case we prepared 50 µl of reaction solution consisting of the following products:

1 µg dsDNA (purified after ligation step)

1× (or 5 µl) CutSmart buffer (initial concentration 10×, catalog #B7204S, NEB)

8 units of AflIII restriction enzyme (initial concentration 20000 units/ml, catalog #R0520S, NEB)

20 µg BSA (Bovin Serum Albumin), Molecular Biology Grade (initial concentration 20 mg/ml, catalog #B9000S, NEB)

Distilled water to adjust the reaction volume to 50 µl (if required).

Then the reaction solution was homogenized by a pipet and was incubated 4 h at 37° C.

After the incubation, the reaction mix was purified using Monarch® PCR & DNA Cleanup Kit (5 µg) (catalog #T1030S, NEB) and was ready for Klenow Fragment (3'→5' exo-) enzyme (catalog #M0212S, NEB) treatment.

A5 Klenow Fragment (Exo-) Treatment

After the restriction of dsDNA by AflIII enxyme, the missing four nucleotides of the lagging strand (5'→3' TTAA) can be filled by another four nucleotides two of which (two adenines) are biotin modified. This filling can be done using Klenow Fragment (3'45' exo-) enzyme (catalog #M0212S, NEB). The recommended reaction volumes are ≤50 µl. 50 µl reaction solution was obtained by preparing a mixture of following products:

1 µg dsDNA (purified after restriction by AflIII enzyme)

3.76 µl Biotin-14-dATP (initial concentration 0.4 mM, catalog #19524-016, Invitrogen 3 µl mix of 1 mM of each: dATP, dTTP, dGTP (catalog #N04465, NEB)

5 µl (1×) NEBuffer 2 (initial concentration 10×, catalog #B7002S, NEB)

6 units of Klenow Fragment (3'→5' exo-) (catalog #M0212S, NEB)

Distilled water to adjust the reaction volume to 50 µl (if required).

The reaction solution was then homogenized by a pipet and was incubated 30' at 37° C.

After incubation the enzyme was heat inactivated by incubating the sample for 20' at 75° C. The sample then was purified by Monarch® PCR & DNA Cleanup Kit (5 µg) (catalog #T1030S).

The IVT of RNA strand and hybridization were done as follows (steps B1-B3):

B1 In Vitro Transcription of RNA Leading Strand

2 µg of purified PCR product was used for in vitro transcription (IVT) of the RNA leading strand using RiboMAX™Large Scale RNA Production Systems (catalog #P1300, Promega). The protocol is as follows. For 50 µl reaction solution the following products were mixed:

2 µg dsDNA (purified PCR product)
10 µl T7 RNA polymerase buffer (5×)
5 µl Enzyme mix (T7)
15 µl rNTP mix (rATP, rGTP, rCTP and rUTP, 25 mM each)
Distilled water to adjust the reaction volume to 50 µl (if required)

The reaction mix was homogenized by a pipet and was incubated 3 h at 37° C.

To eliminate the ssDNA and dsDNA remained in the IVT product, 1.5 µl RQ1 RNase-Free DNase (catalog #M6101, Promega) was added to the reaction solution.

The latter was then incubated 15 min at 37° C. After RQ1 digestion, the IVT product was purified by Monarch® Total RNA Miniprep Kit (catalog #T2010S, NEB, part 2 in the manual starting from step 3) and was ready to be hybridized with DNA lagging strand.

B2 Hybridization

The recommended ssRNA:dsDNA ratio for hybridization is 1.5:1. This means for 1 pmol dsDNA we will need 1.5 pmols ssRNA. The recommended hybridization volume is ≤25 µl. The upper limit (25 µl) was chosen. Hybridization is performed in a special buffer (hybridization buffer), which consists of 50 mM NaCl (catalog #S7653, Sigma-Aldrich)
10 mM Hepes pH 7.6 (Hepes free acid, catalog #391340-25GM, Sigma-Aldrich)
0.5 mM EDTA (catalog #V4231, Promega)
12.5 µl of 100% Formamid (50% of final volume, catalog #F9037, Sigma-Aldrich).

Afterwards the reaction solution was obtained by mixing
1 pmol dsDNA* (purified after Klenow Fragment (3'→5' exo-) treatment)
1.5 pmols ssRNA (purified IVT product)
Hybridization buffer to obtain 25 µl final volume.

The required concentration of dsDNA is usually obtained in big volumes. To avoid adjusting the concentration of the hybridization buffer (in order to obtain 25 µl final volume), it is better to concentrate or even dry the dsDNA beforehand in the reaction tube a using vacuum centrifuge, and then to add ssRNA and the hybridization buffer into the tube.

The final reaction mix was then gently homogenized by a pipet and went through following thermal cycle:
98° C.→1'
65° C.→15'
60° C.→15'
55° C.→5'
50° C.→5'
40° C.→5'
30° C.→5'
20° C.→5'

After hybridization, the remaining in the reaction mix dsDNA and ssDNA were digested using EcoRI-HF® restriction enzyme in 50 µl reaction volume. The new reaction solution consists of:

25 µl reaction mix (after hybridization)
5 µl CutSmart® Buffer (initial concentration 10×, catalog #B7204S, NEB)
1 µl EcoRI-HF® restriction enzyme (initial concentration 20000 units/ml, catalog #R3101S, NEB)
19 µl Distilled water to adjust the reaction volume to 50 µl The restriction was performed incubating the reaction mix 15' at 37° C. EcoRI-HF® was inactivated by a second incubation 20' at 65¶C. The sample was then purified using Microspin™ G-50 Columns (catalog #GE27-5330-01, Sigma-Aldrich) and was obtained a hybrid molecule (RNA-DNA) with biotin modifications at both extremities of DNA lagging strand. This sample was then ready for the final step: the ligation of biotin modified RNA oligonucleotide to RNA 3' extremity.

B3 Ligation of sur_RNAbiot_MB Ph

Ligation of sur_RNAbiot_MB Ph oligonucleotide (5'→3' Phosphate_GCG-CAn-CAG-G, n=biotin-dT 684.70) is performed in 100 µl reaction volume. The reaction mix components are the followings:

1 pmol RNA-DNA hybrid (after hybridization)
0.22 pmols sur_RNAbiot_MB oligonucleotide
10 µl T4 Rnl2 Reaction Buffer (initial concentration 10×, supplied with T4 RNA Ligase 2 (dsRNA Ligase))
70 units of T4 RNA Ligase 2 (dsRNA Ligase, initial concentration 10000 units/ml, catalog #M0239S, NEB)
Distilled water to adjust the reaction volume to 100 µl (if required).

The reaction solution was then gently homogenized by a pipet and was incubated for 4 h at 37° C. After the incubation, the non incorporated biotin modified oligonucleotides were removed by Microspin™ G-50 Columns (catalog #GE27-5330-01, Sigma-Aldrich).

Figure 3:
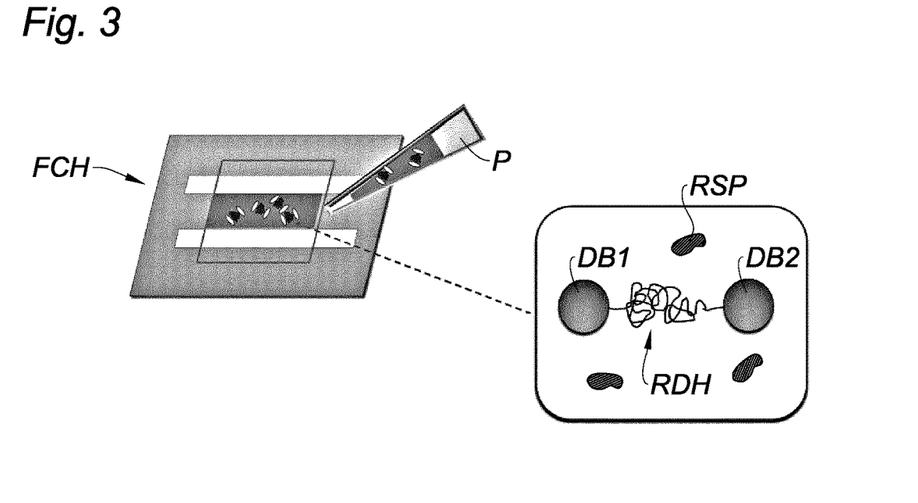
FIG. 3 shows a fluidic chamber of the apparatus of FIG. 2.

Streptavidin-functionalized beads were added, and the solution was introduced in the fluidic chamber FCH using a pipet P, as shown on FIG. 3.

For some experiments, five r-proteins (ribosomal proteins), which have been identified as being essential and sufficient for in vitro formation of the first reconstitution intermediate, $RI_{50}(1)$, and are therefore called "the early binders" or "early essentials" were also added to the solution. They are uL4, uL13, bL20, uL22, uL24.

The rplD, rplM, rplT, rplV or rplX gene encoding uL4, uL13, bL20, uL22 or uL24 from *E. coli* strain A19 were cloned into the pET-15b-SUMO expression vector, possessing $His_6$ tag and SUMO (Small Ubiquitin-like Modifier) downstream the T7 promoter site of pET-15b. The Rosetta (DE3)pLysS derivative carrying the above plasmids were grown in LB containing 100 µg/ml ampicillin and 25 µg/ml chloramphenicol.

Proteins uL4, uL13, bL20, uL22 or uL24 were overexpressed in the *E. coli* strain Rosetta(DE3)pLysS (Novagen) after 3 h IPTG induction at 37° C. Cells overexpressing each recombinant protein were sonicated in lysis buffer (400 mM KCl, 20 mM $MgCl_2$, 50 mM Tris-HCl pH 7.6, 4 M Urea and 7 mM beta-mercaptoethanol for uL4, 100 mM KCl, 10 mM $MgCl_2$, 50 mM Tris-HCl pH 7.6, 7 mM beta-mercaptoethanol for bL20, 1 M $NH_4Cl$, 10 mM $MgCl_2$, 50 mM Tris-HCl pH 7.6, 7 mM beta-mercaptoethanol for uL13, uL22 and uL24) and the extract was centrifuged at 20 000 g for 45 min. After centrifugation, uL4, uL13, uL22 and uL24 were recovered as soluble state. Precipitated bL20 was washed by lysis buffer containing 4% Triton X-100 and refolded in 8 M urea. The proteins were purified by nickel column and digested at the C terminus of the His$_6$ tag-SUMO by protease Ulp1. After reverse his tag purification by nickel column, uL4, uL13, uL22 and uL24 were dialyzed against ion exchange buffer (100 mM KCl, 10 mM MgCl$_2$, 50 mM Tris-HCl, pH 7.6, 4 M Urea and 7 mM beta-mercaptoethanol for uL4, 100 mM KCl, 10 mM MgCl$_2$, 50 mM Tris-HCl, pH 7.6, 2 M Urea and 7 mM beta-mercaptoethanol for uL13 and uL22, 200 mM KCl, 10 mM MgCl$_2$ 50 mM Tris-HCl, pH 7.6, 7 mM beta-mercaptoethanol for uL24) and further purified on MONOS column using a 100-600 mM KCl gradient in uL4, uL13 and uL22, 200-600 mM KCl gradient in uL24. The purity of all proteins was analyzed by SDS-PAGE and confirmed that there are no extra bands. Collected proteins were dialyzed against storage buffer (1 M KCl, 10 mM MgCl$_2$, 50 mM Tris-HCl pH 7.6, 30% glycerol and 7 mM beta-mercaptoethanol for uL4, uL13 and uL22; 1 M KCl, 10 mM MgCl$_2$, 50 mM Tris-HCl pH 7.6, 2 M urea, 30% glycerol and 7 mM beta-mercaptoethanol for bL20; 1 M KCl, 20 mM MgCl2, 50 mM Tris-HCl pH 7.6, 30% glycerol and 7 mM beta-mercaptoethanol for uL24). Aliquots of the proteins were frozen at −80° C.

Protein bL20C, corresponding to amino acids 59-118 of bL20, was prepared as in [Haentjens-Sitri 2008].

Using bL20 protein in single-molecule force measurements is difficult. The protein sticks to the walls of sample chamber and induces adhesion between polystyrene beads thus making force measurements impossible. To overcome this obstacle 23S rRNA was added to the sample before adding bL20 protein. Addition of 23S rRNA at appropriate concentration (0.25 μM for 1 μM bL20 in final experimental volume), fully eliminating the problem. To prepare the 23S rRNA, the sequence of interest (2904 bp) containing the gene rrlB (coding for 23S rRNA) was first amplified by polymerase chain reaction (PCR). One of the two PCR primers is designed to introduce a T7 RNA polymerase promoter sequence at one extremity of PCR product. The polymerase promoter sequence allows to in vitro transcribe the 23S rRNA. Introducing this 23S rRNA in the experimental sample made possible to perform single-molecule force measurements in the presence of all five early essentials at 1 μM each.

Figure 5:
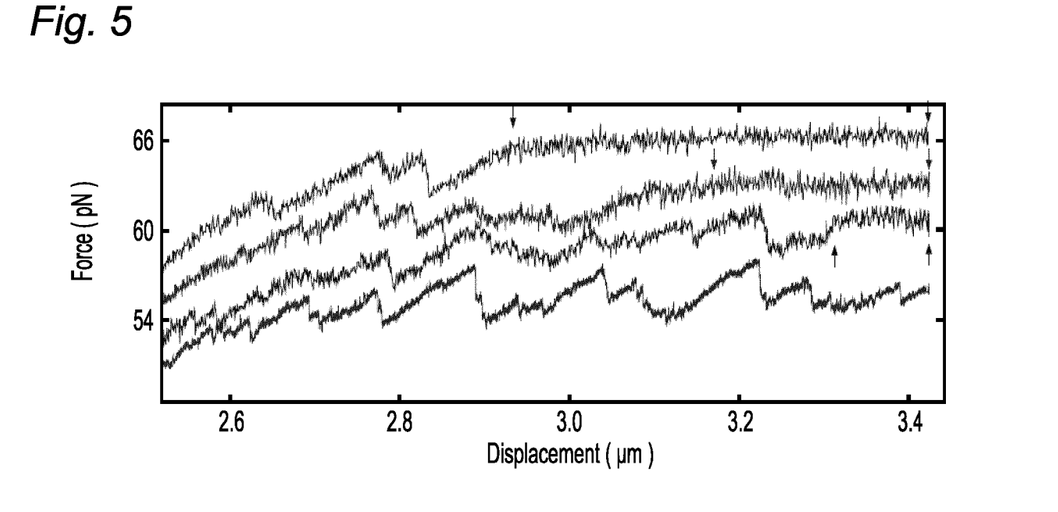
FIGS. 5 to 11 are plots illustrating the technical result of the invention.

FIG. 5 shows different curves corresponding to the force-displacement relationships measured while overstretching of the heteroduplex at different displacement velocities: 10 nm/s; 300 nm/s; 500 nm/s and 750 nm/s (top curve) from bottom to top. Curves other than the bottom one are shifted by 2, 4 and 6 pN, for better visualization. A velocity of 10 nm/s approximately correspond to the average in vivo transcription velocity in the E. coli bacterium.

At the lowest displacement velocity, the curve shows the typical sawtooth-like features of the peeling regime. At higher displacement velocities, some regions of the plateau (represented between arrows) exhibit a smooth force signal, which is associated with an overstretching mechanism non involving peeling. Smooth regions of the curve convey less useful information on inter- and intramolecular interactions involving RNA, therefore they are best avoided by suitably choosing the displacement velocity e.g. between 1 and 300 nm/s and preferably between 5 and 100 nm/s (too low velocities lead to excessively long measurements). Salt, in particular NaCl and MgCl$_2$ concentrations, also affect the appearance of smooth regions (the higher the salt concentration, the lower the displacement velocity at which smooth regions appear; divalent salts like MgCl$_2$ have a stronger effect than monovalent salts like NaCl). The measurements of FIG. 5 were acquired in a buffer solution containing 150 mM NaCl, 10 mM MgCl2, 10 mM Hepes, pH 7.6.

FIGS. 6 to 11 shows force-displacement curves obtained in the absence (FIG. 6) or in the presence (FIGS. 7-11) of early-binding proteins. In all these figures, the black line represents the force measured while stretching the heteroduplex and the gray one the force measured while relaxing it.

Figure 6:
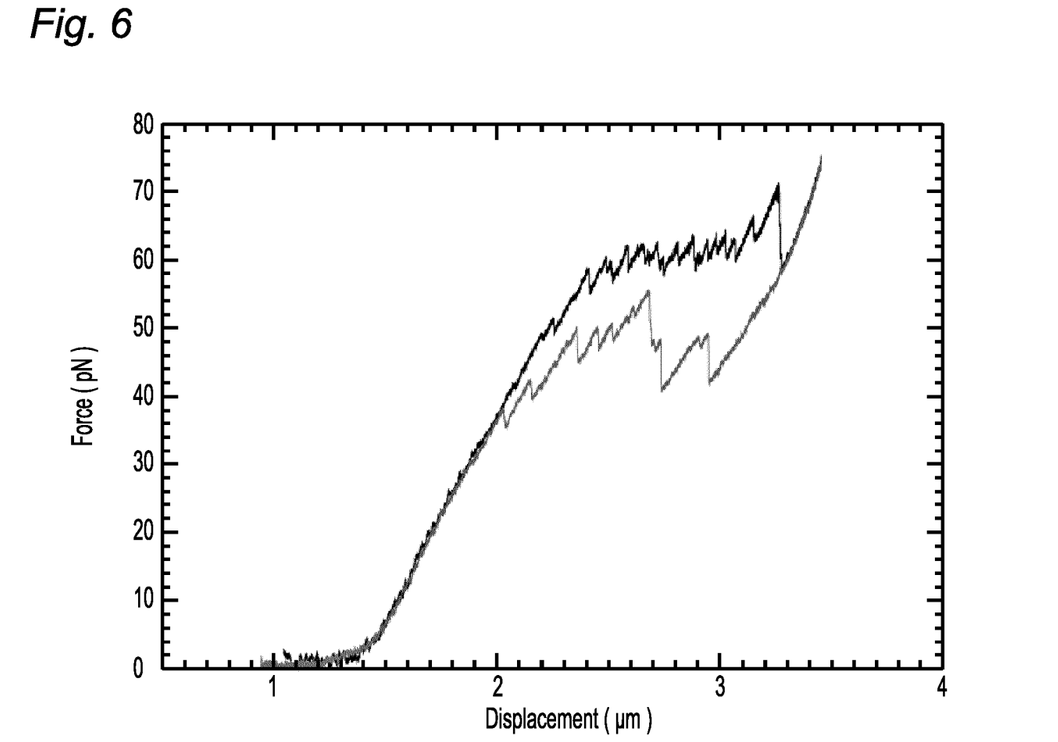

FIG. 6 shows a force-displacement curve obtained in the absence of proteins.

Initially, the displacement increases with a constant velocity of 10 nm/s. A flat response is observed in the low-displacement regime, followed by a significant increase when the imposed displacement approaches the crystallographic length of the molecular construct, which occurs at about 1.5 μm in the present case. Around about 30 pN the curvature changes sign and becomes negative, which is attributed to twist-stretch coupling. Up to these forces, the force-displacement curve can be theoretically described by a twisted worm-like chain model. At about 60 pN starts the overstretching transition, which in this case manifests itself by a plateau with superimposed saw-tooth shaped peaks. The saw-teeth are sequence induced features and are signatures of overstretching of the RNA-DNA heteroduplex by a peeling mechanism. The RNA strand progressively peels off, starting from its 5' end with an average rate corresponding to the in vivo elongation rate of rRNA transcription in E. coli. At the right hand side of the curve, a smooth increase after complete peeling is observed; this part describes the elastic response of the ssDNA under tension.

Afterwards, the movement of the mobile trap is reversed: the displacement decreases with constant velocity of 30 nm/s and heteroduplex re-annealing can occur.

The ssRNA response initially continues down to a force well below the peeling plateau and then evolves by repeated events of sizeable decrease in force followed by sudden increases. The former (latter) correspond to delays (bursts) in re-annealing. A delay is expected when the RNA single strand contains a stable structure that must melt before the heteroduplex can reform. Significant variability in the number and positions of the delays was found, indicating that the re-annealing occurs in a stochastic manner. Around 35 pN the curve joins the curve measured upon increasing displacement and closely follows the latter down to zero-force.

In the presence of an increasing number of early-binding proteins, complete re-annealing is not always achieved during the ramp of decreasing trap distance. A measurement showing the signatures of partial re-annealing is presented in FIG. 7, which corresponds to a cycle of peeling and re-annealing in the presence of uL4 and uL24 at 8 μM each. This figure shows (i) hysteresis between the curves recorded upon peeling and re-annealing, and (ii) crossing of the curves at low force. A partially-annealed construct is composed of a double-stranded part (the re-annealed fraction) in series with a single-stranded part (the non-re-annealed fraction). At low extension, a DNA single-strand of N-nucleotides exhibits higher force than an RNA-DNA double-strand of N basepairs. The crossing is thus attributed to the fact that a DNA single-strand is shorter than an RNA-DNA hybrid at low force, while the opposite holds at high force.

A statistical analysis was performed, selecting occurrence of the crossing at low force as criterion for partial annealing. Measurements with the 23S RNA alone and with the RNA plus early-binding proteins were compared. A cycle of peeling and subsequent re-annealing was taken into account in this analysis if it was the first force-measurement cycle performed on the molecule or when the immediately preceding cycle clearly showed full annealing of the heteroduplex. Proteins increase the probability of observing a crossing at low force increases by more than a factor of three—from 17.9% without proteins to 62.5% with 8 µM each of uL4 and uL24. This was attributed to an efficient stabilization of structure within the peeled rRNA. It was recently shown in vitro by single-molecule force measurements that the assembly initiator uL24 and the essential protein uL4 cooperatively bind and mechanically stabilize a region of domain I, consisting of helices H18, H19 and H20 (unpublished results). It can therefore be concluded that the two proteins act as folding helpers in the present in vitro assay that mimics the co-transcriptional folding happening in vivo.

The measurements were then extended to study the effect of the early essentials at concentrations of 1 µM each, since in vitro reconstitution of the E. coli large ribosomal subunit involves protein concentrations of about 1 µM. The results are:

No protein: crossing probability 17.9%
L4, L24, 1 µM each: 27.9%
L4, L24, L22, L13, 1 µM each: 31.75%
L4, L24, L22, L13, L20C, 1 µM each: 45.2%

The probabilities were determined based on 67, 24, 63 and 31 individual cycles of peeling and re-annealing, respectively.

Figure 7:
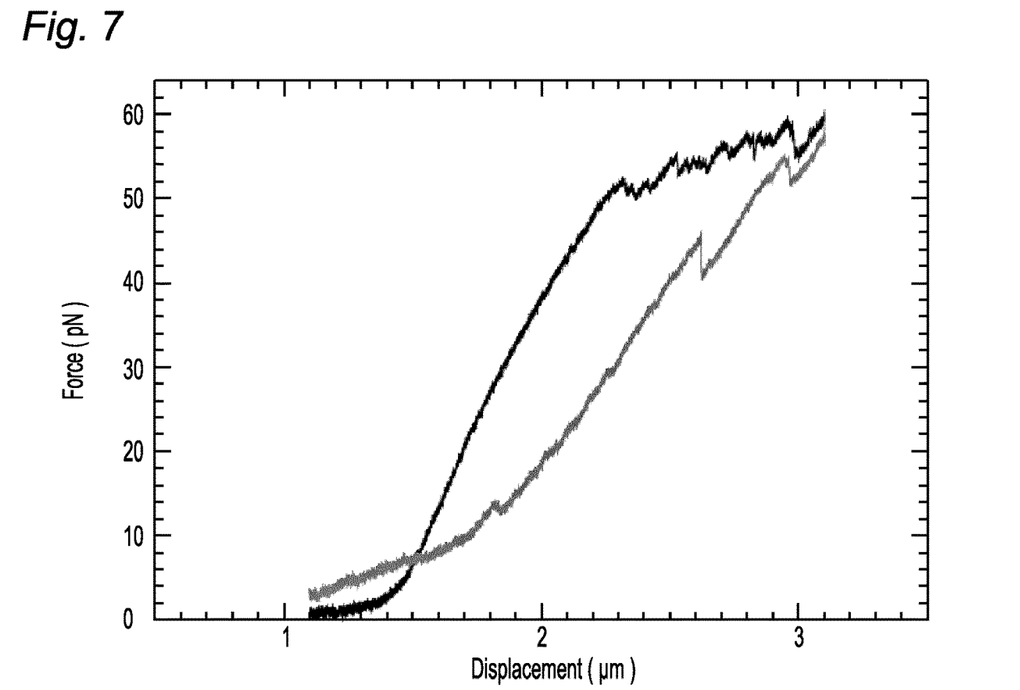

At this lower protein concentration, presence of uL4 and uL24 still significantly increases the fraction of partial annealing, although the effect is smaller than in the higher concentration case of FIG. 7. Addition of uL22, uL13 and bL20C increased the percentage, in agreement with the established view that the early essentials act together to rapidly form the first reconstitution intermediate $RI_{50}$ (1).

Starting from the ensemble uL4+uL24+uL22+uL13, the effect of bL20 in comparison with bL20C was investigated. As discussed above, using bL20 protein in these experiments is tricky, since the full-length bL20 protein sticks to the walls of the sample chamber and induces adhesion between polystyrene beads thus making force measurements impossible, but the obstacle was overcome by adding 23S rRNA to our experimental sample before adding bL20 protein. This allowed performing single-molecule force measurements in the presence of all five early essentials at 1 µM each.

Measurements with all five early essentials uL4+uL24+uL22+uL13+bL20 reveal three distinct behaviors which can be called "full anneal", "partial anneal" and "no anneal", respectively and have already discussed in reference to FIGS. 1C-1E. Force measurements performed with the full set of early binding proteins are shown in FIGS. 8-11. They illustrate the no anneal (FIG. 8), the partial anneal (FIG. 9 and FIG. 10) and the full anneal (FIG. 11) cases.

With no proteins, full annealing was observed in 60% of 30 analyzed stretch-release cycles, partial annealing in 40% of cases and no annealing was not observed.

With uL4, uL13, uL22, uL24 and bL20C, full annealing was observed in 25% of 20 analyzed stretch-release cycles, partial annealing in 55% of cases and no annealing in 20% of cases.

With uL4, uL13, uL22, uL24 and bL20, full annealing was observed in 22% of 50 analyzed cycles, partial annealing in 34% of cases and no annealing in 44% of cases.

In the presence of proteins, their concentrations were 1 µM each. Stretching was performed with a displacement velocity of 10 nm/s, mimicking the vectorial 5' to 3' generation of the rRNA with a rate of 40 nt/s as it occurs in E. coli.

These results show that the five early essentials efficiently stabilise the peeled 23S rRNA, which supports the hypothesis of an assembly gradient. While the no-anneal fraction has a clear majority presence in the no-protein case, no-anneal is minority for both cases with proteins. Stronger stabilization occurs in the presence of bL20 than with bL20C: the replacement of bL20C by bL20 more than doubles the "no anneal" fraction and slightly reduces the "full anneal" fraction. The stronger stabilization in the presence of bL20 suggests that the n-terminal part of bL20 plays a non-negligible role during the transcription of domain I and II, i.e. already within the early-stage of ribosome assembly.

Figure 8:
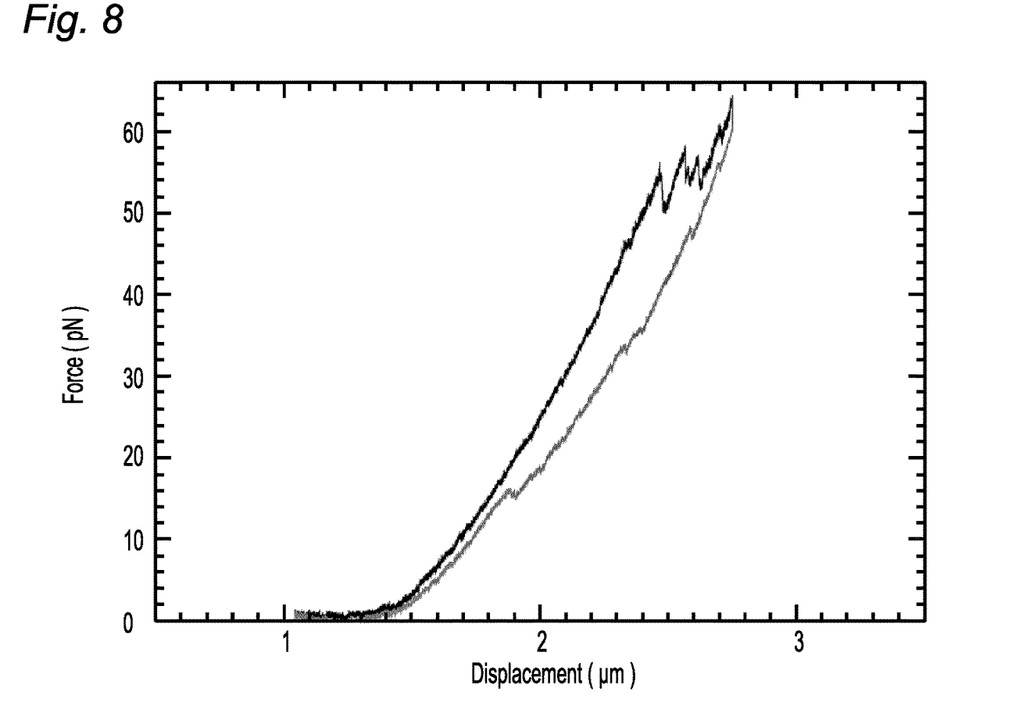

More particularly:

FIG. 8 corresponds to a stretch-release cycle performed on the molecular construct in the presence of the five early binders. The direction of displacement is returned after an overstretching plateau of 300 nm, which corresponds to peeling the first about 1200 nucleotides at the 5' end of the 23S rRNA. Upon relaxation, the measured force decreases without noteable events of sudden return, in striking contrast to the cycle present in FIG. 6. This behaviour was classified as "no anneal". The blocking observed in this case is attributed to formation of the nt 991-1163 substructure of Domain II, which encompasses helices 40 to 44 and was previously shown to be mechanically stabilized by bL20. The same substructure contains a major binding site of uL13.

Figure 9:
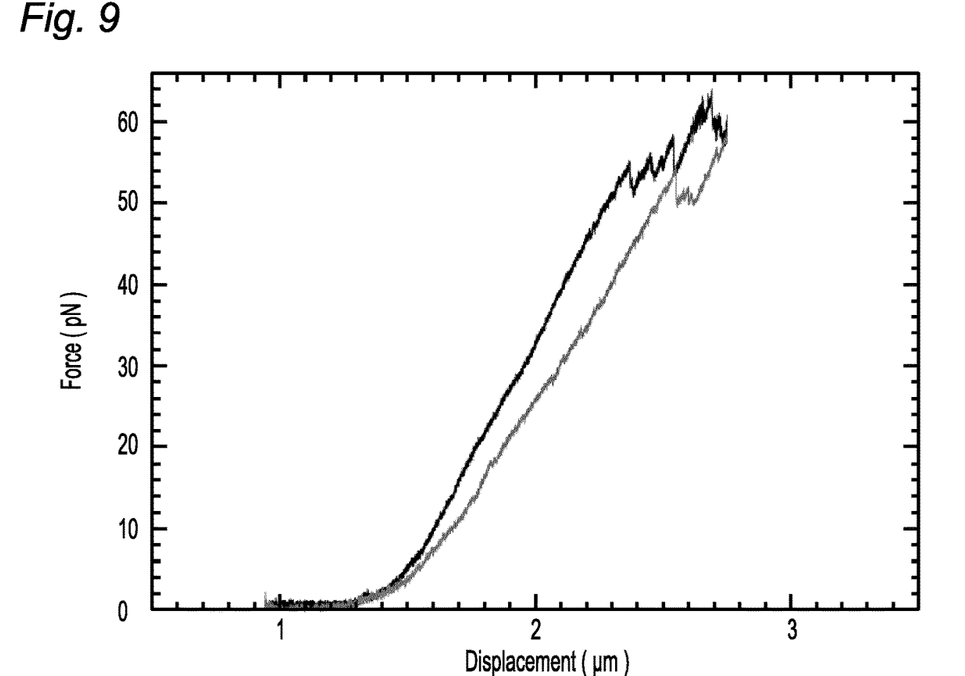

FIG. 9 presents another stretch-release cycle performed on the molecular construct in the presence of the five early binders. In this case, the curves measured for increasing and decreasing displacement join (at a displacement of about 2.5 µm), which indicates full annealing of the RNA sequence that is peeled last. This sequence is located at the 3'-side of the peeled single-stranded RNA and roughly corresponds to nucleotides 900-1500 of the 23S RNA. Below this value of displacement, distinct upwards jumps in force are not observed. Rather, force decreases in a monotonic manner down to zero, which indicates that a structure is present in the peeled rRNA that is sufficiently stable to prevent further re-annealing. This behaviour was classified as "partial anneal". The blocking occurs around nt 900 in this case, which would be compatible with the particularly long and GC-rich helix formed by nt 838-940 of the 23S RNA. This stable RNA structure might be further stabilized by the early-binding proteins (although it does not contain a specific ribosomal-protein binding site).

Figure 10:
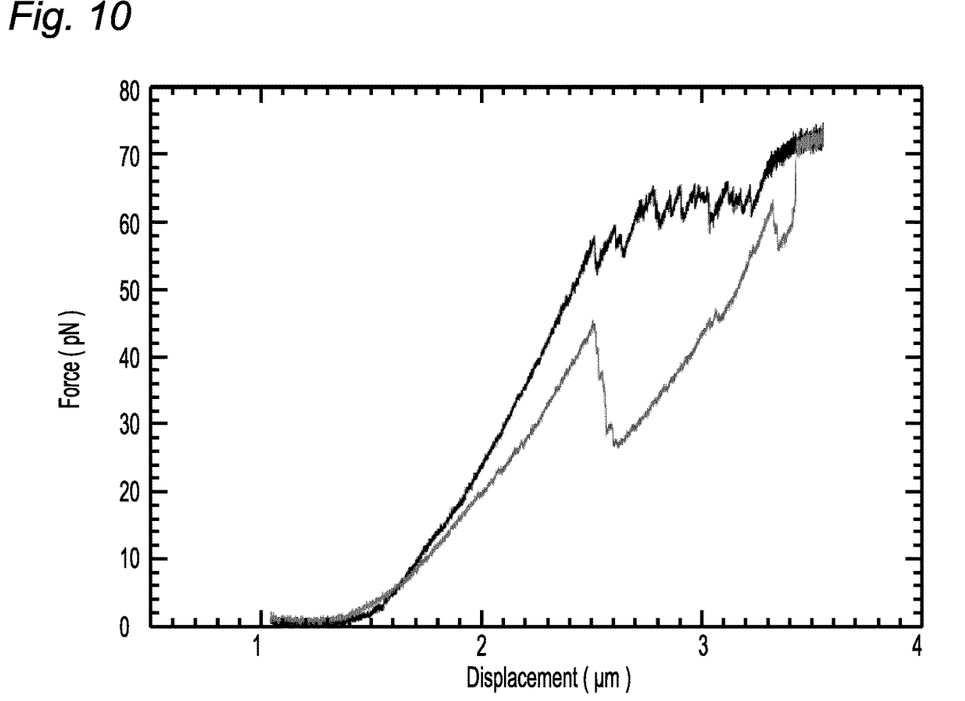

FIG. 10 corresponds to another "partial anneal" cycle, measured in the presence of the five early essentials. The presented cycle directly followed a previous measurement that showed "full anneal". Here, a displacement of about 1050 nm was imposed relative to the onset of the peeling; which normally is enough to peel the entire sequence of our construct. However at an absolute displacement of about 3.2 µm, an increase in force is observed leading to a last part of the curve showing smooth overstretching. For overstretching double-stranded DNA, it was previously shown that smooth overstretching can occur preferentially in GC-rich regions. Indeed, the RNA strand of interest contains a corresponding sequence region with very high local GC-content (79%, determined by computing a sliding average over 40 base pairs, around nt3250). The return trace of this graph does not join the one measured for increasing displacement and displays a crossing at low force (as described in FIG. 7).

Figure 11:
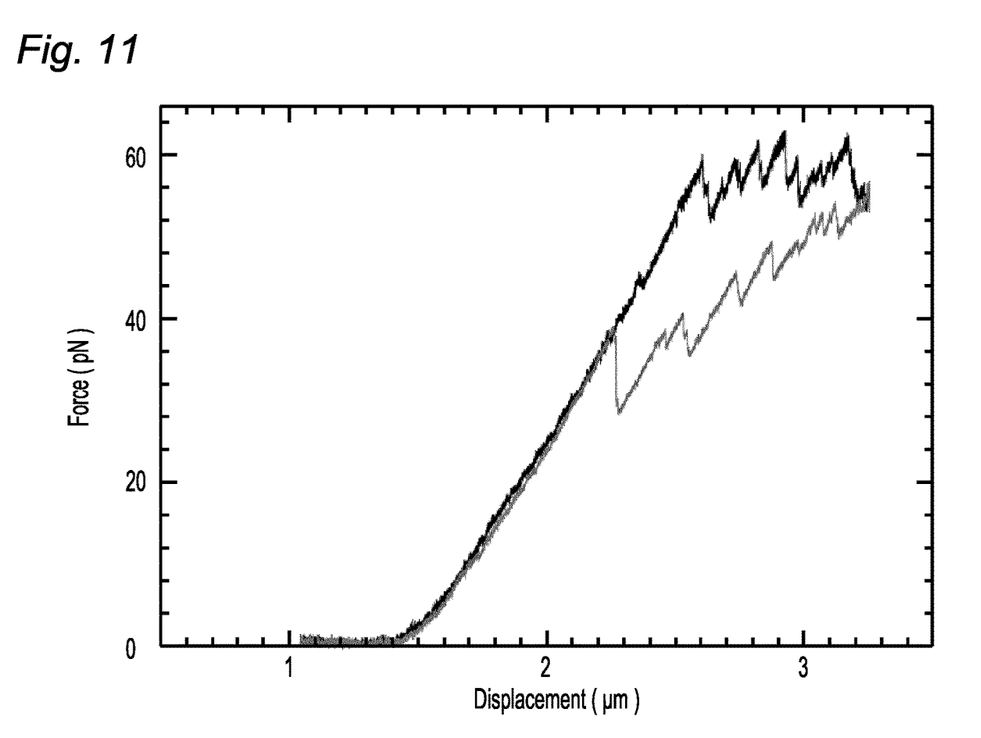

FIG. 11 corresponds to yet another stretch-release cycle measured in the presence of the five early essentials. Here the displacement imposed after the peeling started was about 640 nm, corresponding to about 2570 nt. Nucleotide 2570 lies in domain V of the 23S RNA. This measurement illustrates that full annealing sometimes occurs even if all five early-binding r-proteins are present in the solution at a concentration of 1 μM each and transcription is mimicked to proceed to 88% of the full-length sequence of the 23S rRNA.

The embodiment described above was only provided as a non-limiting example.

The inventive method is not limited to the investigation of ribosome assembly, but can be applied more generally to the investigation of any intra- or inter-molecular interaction affecting the folding of a RNA single strand. In particular, the invention may be applied to the pre-clinical screening of candidate RNA-targeting drugs such as e.g. antibiotics.

Different theoretical models may be used for interpreting the measured force-displacement relationships and deriving information on intra- or inter-molecular interactions. The data analysis may be performed by an investigator or be partially or wholly automated by the use of suitable software.

Any suitable protocol, known from the person skilled in the arts of biochemistry and molecular biology, may be used to synthesize and prepare the RNA/DNA heteroduplex.

The inventive method may be carried out in conditions (chemical environment, temperature, displacement velocity . . . ) mimicking those encountered in vivo, or in different conditions. For instance, it may be interesting to investigate the influence of different salt concentrations, pH, temperature, displacement velocity etc., or even to make the RNA strand peel off from its 3' extremity.

In the embodiments described above, one optical trap is displaced at a constant velocity with respect to the other one. This does not correspond to a constant relative velocity of the opposing ends of the heteroduplex (and therefore of the dielectric beads) because of "stick" and "slip" phases during peeling and annealing. A truly constant peeling/annealing velocity can be obtained by performing a closed-loop control of the nanoscale manipulating device, e.g. using the electronic data processing system EDPS. The control variable may advantageously be the distance between the dielectric beads.

More generally, the displacement of the optical traps and/or the end-to-end distance of the heteroduplex may follow any desired time law, not necessarily a linear one. It is important, however, that the displacement speed be sufficiently low to allow the force-displacement relationship to show the sawtooth-like features, as underlined by FIG. 5, e.g. speeds between 1 and 300 nm/s and preferably between 5 and 100 nm/s.

Optical traps are not an essential element of the invention, and other nanoscale manipulating devices could also be used. However, it is important that at least one of the peeling and the annealing steps (and preferably both) be carried out by imposing a displacement of the ends of the heteroduplex and measuring the corresponding force, and not the other way round. In [Zhang et al. 2019] a magnetic trap has been used to impose a force between the ends of the heteroduplex following a predetermined time law. In these conditions, no sawtooth-like features have been detected, making the method unsuitable to study inter- or intramolecular interactions involving RNA (which, in any case, was not the aim of the author of the paper).

Steps c) and d) are not necessarily carried out in a strictly sequential way, i.e. by monotonously pulling the traps apart and then monotonously pushing them together. Instead, the two steps may be interleaved. For instance the method may comprise a first phase wherein small "forward" displacements of a trap, to peel a portion of the RNA strand, alternate with even smaller "backward" displacements, to partially anneal it, until the RNA strand is completely peeled; and a second phase wherein small "backward" displacement alternates with smaller "forward" ones. This can be helpful in determining precisely the RNA site at which a molecule binds.

The force-displacement measurement may be combined with other measurement and/or imaging techniques such as, but not limited to, confocal fluorescence microscopy or STED.

The apparatus of FIG. 2 has only been described as an example—other apparatuses are known for generating dual-trap optical tweezers, and are suitable to be used for carrying out the invention. Also, the invention is not limited to the use of dual-trap optical tweezers: any other suitable nanoscale manipulating device (i.e. a device able to cause controlled displacements with a resolution lower than 1 μm and preferably lower than 100 nm) can be used to implement the invention. Alternatives to dual-trap optical tweezers are, for instance:

single-trap optical tweezers (one extremity of the heteroduplex being bound to a dielectric bead of the tweezers and the opposite end to a fixed element such as a microscope plate);
magnetic tweezers;
micropipettes;
Atomic Force Microscope (AFM) probes;
nanopores;
etc.

See [Bockelmann 2004] and [Neuman 2007] for more details (and [Laszlo 2016] for a nanopore tool).

REFERENCES

[Lewicki 1993] B. T. U. Lewicki, T. Margus, J. Remme, K. H. Nierhaus«Coupling of rRNA transcription and ribosomal assembly in vivo". J. Mol. Biol. 231, 581-593 (1993)

[Gross et al. 2011]: P. Gross et al. "Quantifying how DNA stretches, melts and changes twist under tension», Nature Physics, Vol. 7, pages 731-735, September 2011.

[Bockelmann 1997]: U. Bockelmann et al. "Molecular stick_slip motion revealed by opening DNA with piconewton forces". Phys. Rev. Lett. 79, 4489_4492 (1997).

[Bockelmann 2002]: U. Bockelmann et al. "Unzipping DNA with optical tweezers: High sequence sensitivity and force flips" Biophys. J. 82, 1537_1553 (2002).

[Smith 1996]: S. B. Smith et al. "Overstretching B-DNA: the elastic response of individual double-stranded and single-stranded DNA molecules" Science 271, 795-799 (1996).

[Wang 1997]: M. D. Wang et al. "Stretching DNA with optical tweezers" Biophys. J 72, 1335-1346 (1997).

[Odijk 1995]: T. Odijk "Stiff Chains and Filaments under Tension. Macromolecules 28, 7016-7018 (1995).

[Mangeol 2008]: P. Mangeol, U. Bockelmann "Interference and crosstalk in double optical tweezers using a single laser source", Review of Scientific Instruments, 79, 083103 (2008).

[Heller 2013]: I. Heller et al. "STED nanoscopy combined with optical tweezers reveals protein dynamics on densely covered DNA", Nature Methods, Vol. 10, No. 9, pages 910-916, September 2013.

[Haentjens-Sitri 2008] Haentjens-Sitri J et al. (2008) "A competition mechanism regulates the translation of the *Escherichia coli* operon encoding ribosomal proteins L35 and L20" J Mol Biol 375: 612-625.

[Bockelmann 2004]: U. Bockelmann "Single-molecule manipulation of nucleic acids", Current Opinion in Structural Biolog, 2004, 14:368-373.

[Neuman 2007]: K. C. Neuman et al. "Single-Molecule Micromanipulation Techniques", Annu. Rev. Mater. Res. 2007.37:33-67.

[Laszlo 2016]: A. H. Laszlo et al. "MspA nanopore as a single-molecule tool: From sequencing to SPRINT", Methods 105 (2016), 75-89.

[Zhang et al. 2019]: Chen Zhang et al. "The Mechanical Properties of RNA-DNA Hybrid Duplex Stretched by Magnetic Tweezers", Biophisical Journal 116, 196-204, Jan. 22, 2019 (published online Dec. 13, 2018).

The invention claimed is:

1. A method for investigating intra- and/or intermolecular interactions involving RNA, the method comprising the steps of:
   a) synthesizing a RNA/DNA heteroduplex comprising a RNA strand of interest paired to a DNA strand, each of said strands having a first and a second end;
   b) binding a first end of the DNA strand and a corresponding first end of the RNA strand to a first element of a nanoscale manipulating device, and a second end of the DNA strand to a second element of the nanoscale manipulating device, leaving a second end of the RNA strand free;
   c) moving the first and second elements of the manipulating device apart from each other, stretching the DNA strand and causing the RNA strand to peel off the heteroduplex, while measuring a force-displacement relationship; and
   d) moving the first and second elements of the nanoscale manipulating device towards each other, allowing the DNA strand to relax and causing the RNA strand to bind again to it, while continuing measuring the force-displacement relationship;
   wherein at least one of step c) and d) is carried out while controlling said moving of the first and second elements of the manipulating device in such a way that an end-to-end distance of the heteroduplex varies according to a predetermined time law, the force-displacement relationship measured during steps c) and d) providing information on intra- and/or intermolecular interactions involving the RNA strand.

2. The method of claim 1 wherein at least step c) is carried out in a medium containing molecules suitable to bind to the RNA strand.

3. The method of claim 2, wherein at least some of said molecules are fluorescent or marked with a fluorophore, and wherein at least one of step c) or step d) comprises exciting a fluorescent emission of said molecule or fluorophores and acquiring a plurality of images of the heteroduplex corresponding to different relative displacements of the first and second elements of the nanoscale manipulating device.

4. The method of claim 2, wherein at least some of said molecules are fluorescent or marked with a fluorophore, further comprising exciting a fluorescent emission of said molecule or fluorophores and acquiring at least one image of the heteroduplex while or after carrying out at least one of said steps c) and d).

5. The method of claim 2, wherein said molecules are chosen among ribosomal proteins, non-ribosomal proteins, small RNAs, and RNA-targeting drugs or drug candidates.

6. The method of claim 1, wherein the first end of the RNA strand is a 3' end and the second end of the RNA strand is a 5' end.

7. The method of claim 1, wherein during steps c) and d), the first and second elements of the manipulating device are moved with relative displacement speeds comprised between 1 and 300 nm/s.

8. The method of claim 1, wherein the nanoscale manipulating device comprises dual-trap optical tweezers, and the first and second parts to which the first and second ends of the DNA strands and the first end of the RNA strand are bound are dielectric beads of said tweezers.

9. The method of claim 1, further comprising a step e) of:
   e1) establishing a correspondence between relative displacement values of the first and second elements of the nanoscale manipulating device and regions of the RNA strand by analyzing the portion of the force-displacement relationship measured during step c); and
   e2) extracting information on intra- and/or intermolecular interactions involving the RNA strand from a comparison of the portion of the force-displacement relationship measured during step c) and of the portion of the force-displacement relationship measured during step d), and from said correspondence between relative displacement values of the first and second elements of the nanoscale manipulating device and regions of the RNA strand.

10. The method of claim 1, wherein steps c) and d) are carried out a plurality of times, information on intra- and/or intermolecular interactions involving the RNA strand being provided by a statistical study of the corresponding force-displacement relationships.

11. The method of claim 1, wherein said moving of the first and second elements of the manipulating device is performed at a displacement velocity sufficiently low to allow the force-displacement relationship to show sawtooth-like features.

* * * * *

SEQUENCE LISTING

```
<160> NUMBER OF SEQ ID NOS: 4

<210> SEQ ID NO 1
<211> LENGTH: 55
<212> TYPE: DNA
<213> ORGANISM: Artificial Sequence
<220> FEATURE:
<223> OTHER INFORMATION: F_MB Forward primer

<400> SEQUENCE: 1
taatacgact cactataggg agacaattgc ttaagggtta agcgactaag cgtac          55

<210> SEQ ID NO 2
<211> LENGTH: 49
<212> TYPE: DNA
<213> ORGANISM: Artificial Sequence
<220> FEATURE:
<223> OTHER INFORMATION: R_MB reverse primer

<400> SEQUENCE: 2
ccactgaatt gagcagaccc ggccggagag gatcgatcag actaatcat                49

<210> SEQ ID NO 3
<211> LENGTH: 36
<212> TYPE: DNA
<213> ORGANISM: Artificial Sequence
<220> FEATURE:
<223> OTHER INFORMATION: sur_DNAbiot_MB
<220> FEATURE:
<221> NAME/KEY: misc_feature
<222> LOCATION: (31)..(31)
<223> OTHER INFORMATION: n is biotin-dT 684.70 (Eurofins Genomics)
<220> FEATURE:
<221> NAME/KEY: misc_feature
<222> LOCATION: (36)..(36)
<223> OTHER INFORMATION: n is biotin-dT 684.70 (Eurofins Genomics)

<400> SEQUENCE: 3
cctctcctag ctagtctgat tagtagcgca ncaggn                              36

<210> SEQ ID NO 4
<211> LENGTH: 40
<212> TYPE: DNA
<213> ORGANISM: Artificial Sequence
<220> FEATURE:
<223> OTHER INFORMATION: sur_compDNA2biot_MB
<220> FEATURE:
<221> NAME/KEY: misc_feature
<222> LOCATION: (34)..(34)
<223> OTHER INFORMATION: n is biotin-dT 684.70 (Eurofins Genomics)
<220> FEATURE:
<221> NAME/KEY: misc_feature
<222> LOCATION: (37)..(37)
<223> OTHER INFORMATION: n is biotin-dT 684.70 (Eurofins Genomics)
<220> FEATURE:
```

```
<221> NAME/KEY: misc_feature
<222> LOCATION: (40)..(40)
<223> OTHER INFORMATION: n is biotin-dT 684.70 (Eurofins Genomics)

<400> SEQUENCE: 4
ggccggagag gatcgatcag actaatcatc gcgnagnccn                              40
```